United States Patent [19]

Bussell

[11] Patent Number: 6,017,912

[45] Date of Patent: Jan. 25, 2000

[54] TOPICAL FLUOROQUINOLONE ANTIBIOTICS IN AN ALCOHOL AND ACETONE VEHICLE

[76] Inventor: Letantia Bussell, 433 N. Camden Dr., Suite 805, Beverly Hills, Calif. 90210

[21] Appl. No.: 09/031,862

[22] Filed: Feb. 27, 1998

[51] Int. Cl.[7] .................. A61K 31/535; A61K 31/495; A61K 31/47; A61K 31/44

[52] U.S. Cl. .................. 514/230.2; 514/253; 514/254; 514/300; 514/312

[58] Field of Search .................. 514/230.2, 253, 514/254, 300, 312

[56] References Cited

PUBLICATIONS

Remington' Pharmaceutical Sciences, 15th edition, pp. 1252–1253, 1975.

*Primary Examiner*—Phyllis G. Spivack

[57] ABSTRACT

A method of treating bacterial infections of the skin comprising topically administering a pharmaceutical composition comprising fluoroquinolones selected from the group consisting of ciprofloxacin, ofloxacin, enoxacin, cinoxacin, pefloxacin, lomefloxacin, norfloxacin, tosufloxacin, fleroxacin, temafloxacin, trovafloxacin and difloxacin, mixed in an alcohol acetone vehicle is disclosed. The topical carrier will be in the form of a cream, ointment, lotion, gel, suspension, emulsion, cleansing bar, pledget, salve, tincture, spray, transdermal device, or other appropriate non-toxic pharmaceutical vehicle.

5 Claims, No Drawings

TOPICAL FLUOROQUINOLONE ANTIBIOTICS IN AN ALCOHOL AND ACETONE VEHICLE

BACKGROUND OF THE INVENTION

This invention relates to the topical application of all fluoroquinolones, including but not limited to, ciprofloxacin, ofloxacin, enoxacin, cinoxacin, pefloxacin, lomefloxacin, norfloxacin, tosufloxacin, fleroxacin, temafloxacin, trovafloxacin, and difloxacin, mixed in an alcohol and acetone vehicle for the treatment of a variety of organisms which infect the skin and a variety of inflammatory skin conditions. It will be in the form of a cream, ointment, lotion, gel, suspension, emulsion, cleansing bar, pledget, salve, tincture, spray, transdermal device, or other appropriate non-toxic pharmaceutical carrier.

Fluoroquinolone antibiotics were first developed in the early 1960s but the earliest one, nalidixic acid, proved particularly susceptible to resistant bacteria thereby making it ineffectual over the long term. In the last five years, fluoroquinolones have become increasingly popular as chemical alterations have dramatically decreased the resistant bacteria appearing after treatment. This has made the family of fluoroquinolones more effective than a number of other antibiotics in combating bacterial infections. Fluoroquinolones attack bacteria by targeting DNA gyrase and by interfering with bacterial replication.

Theses antibiotics have been used extensively to treat respiratory tract infections, urinary tract infections, diarrhea, postoperative-wound infections, and many other conditions, because they are readily absorbed after oral and topical administration and exhibit potent in vitro activity against a broad spectrum of bacterial species. U.S. Pat. No. 5,476,854 describes the oral, intravenous and transdermal use of lomefloxacin to treat urinary tract infections, upper respiratory tract infections, sexually-transmitted infections, opthalmological infections and intestinal infections.

Fluoroquinolone antibiotics are active against a wide spectrum of gram-positive and gram-negative bacteria because of their broad antimicrobial activity. Varieties of fluoroquinolones, specifically ciprofloxacin, have been found to be effective against *Staphylococcus aureus, Streptococcus pneumoniae,* coagulese-negative *staphylococci, Streptococcus pyogenes, Staphylococcus epidermis, Pseudomonas aeruginosa, Escherichia coli, Klebsiella pneumoniae, Enterobacter cloacae, Proteus mirabilis, Proteus vulgaris, Providencia stuartii, Morganella morganii, Citrobacter diversus, Citrobacter freundii,* and other susceptible organisms. The mounting resistance of Staphylococcus aureus to both penicillin and erythromycin has made the fluoroquinolone antibiotics a viable alternative for the treatment of skin diseases. Studies of the effectiveness of the oral treatment of ciproflaxacin on skin and soft tissue infections have shown the medicine to have cure rates of 80% to 100%.

Topical compositions of fluoroquinolones and its derivatives have been used for opthalmic use, as seen in U.S. Pat. No. 4,551,456, which describes the use of norfiloxacin and related antibiotics in the topical treatment of ocular infections. U.S. Pat. No. 5,374,432 describes a topical composition chosen from aminoglycoside antibiotics and quinolone antibiotics mixed in a sterile carrier, such as a water or ointment base, for the treatment of burns, other infection-prone wounds and ocular infection. U.S. Pat. No. 5,401,741 describes the topical treatment of ofloxacin mixed in an aqueous solution, for otopathy.

Combining a fluoroquinolone with a second active ingredient or antibiotic utilizes the two drugs' different mechanisms simultaneously to attack the many varieties of skin infections, inflammations and diseases. Fluoroquinolones have been tested in combination with coumermycin, amikacin, oxacillin, gentamicin, vanomycin, azlocillin, rifampin, and fosfomycin and have shown different degrees of synergy against *Staphylococcus aureus.* U.S. Pat. Nos. 3,944,668 and 4,038,388, combine tetracycline with 8-hydroxyquinoline in a topical or oral application as the two active ingredients behave synergistically against certain micro-organisms. U.S. Pat. No. 5,648,389 describes a topical composition mixing an antimicrobial, including ciprofloxacin, with a beta hydroxy acid and water soluble zinc compound to treat acne in humans.

The objective of this invention is to combine all fluoroquinolones, including but not limited to, ciprofloxacin, ofloxacin, enoxacin, cinoxacin, pefloxacin, lomefloxacin, norfiloxacin, tosufloxacin, fleroxacin, temafloxacin, trovafloxacin, and difloxacin, in an alcohol and acetone vehicle for the topical treatment of a variety of skin conditions. The composition will be in the form of a cream, ointment, lotion, gel, suspension, emulsion, cleansing bar, pledget, salve, tincture, spray, transdermal device, or other appropriate non-toxic pharmaceutical carrier.

OTHER REFERENCES CITED

Brody, Terri., and Myles L. Pensak, "The Fluoroquinolones," *The American Journal of Otology,* vol. 12, no. 6, pp. 477–479, November 1991.

Douidar, Samir M., and Wayne R. Snodgrass, "Potential Role of Fluoroquinolones in Pediatric Infections," *Reviews of Infectious Diseases,* vol. 11, no. 6, pp. 878–889, November–December 1989.

Fong, I. W., "The Role of Fluoroquinolones in the Management of Skin, Soft Tissue, and Bone Infections," *Clinical and Investigative Medicine,* vol. 12, no. 1, pp. 44–49, 1989.

Guay, David R., "The Role of Fluoroquinolones," *Pharmacotherapy,* supplement to vol. 12, no. 6, pp. 71S–85S, 1992.

Neu, Harold C., "Use of Fluoroquinolone Antimicrobial Agents by Cardiovascular and Cardiopulmonary Surgeons," *Texas Heart Institute Journal,* vol. 17, no. 1, pp. 12–21, 1990.

Neu, Harold C., "Synergy of Fluoroquinolones with Other Antimicrobial Agents," *Reviews of Infectious Diseases,* vol. 11, suppl. 5, pp. S1025–S1035, July–August 1989.

Nolen, Thomas M., "Clinical Trials of Cefprozil for Treatment of Skin and Skin-Structure Infections: Review," Clinical Infectious Diseases, vol. 14(Suppl 2), pp. S255–263, 1992.

Powers, Robert D., Robert Schwartz, Rodney M. Snow, and Dabney R. Yarbrough III, "Ofloxacin versus Cephalaxin in the Treatment of Skin, Skin Structure, and Soft-Tissue Infections in Adults," *Clinical Therapeutics,* vol. 13, no. 6, pp. 727–736, 1991.

Rodriguez, William J., and Bernhard L. Wiedermann, "The Role of Newer Oral Cephalosporins, Fluoroquinolones, and Macrolides in the Treatment of Pediatric Infections," *Advances in Pediatric Infectious Diseases,* vol. 9, pp. 125–159, 1994.

Talley, Joseph H., "Fluoroquinolones: New Miracle Drugs?" *Postgraduate Medicine,* vol. 89, no. 1, pp. 101–103, 106–108, 111–113, January 1991.

DESCRIPTION OF THE INVENTION

While the invention will be described in connection with a preferred embodiment and method, it will be understood that I do not intend to limit the invention to the embodiment or method. On the contrary, I intend to cover all alternatives, modifications, and equivalents as may be included within the spirit and scope of the invention as defined by the appended claims.

In accordance with the present invention, the selected fluoroquinolone antibiotic in combination in an alcohol and acetone vehicle in the form of an ointment, lotion, cream, gel, suspension, emulsion, cleansing bar, pledget, salve, tincture, spray, transdermal device, or other appropriate non-toxic pharmaceutical carrier. As stated above, the resulting composition is used for the topical treatment of a variety of skin infections conditions.

Compositions are prepared by mixing a selected fluoroquinolone antibiotic as an active ingredient with an alcohol and acetone vehicle. In this solution, a fluoroquinolone antibiotic will be added to an independent mixture of acetone, alcohol and water whereby the fluoroquinolone retains its medicinal properties and allows for the topical administration of the antibiotic.

In the following compositions, "Active Ingredient," means any selected fluoroquinolone antibiotic. The respective concentrations of any of the ingredients can vary (0.1% to 99.0%, for example) as different strengths of the composition are produced. The inactive ingredients are representative only and may vary according to need. Various preservatives (such as benzoic acid) will also be added as needed. These preparations describe the manner and processing of using this invention and are to be construed as exemplary embodiments of the inventive concept and not as limitations thereof.

|  | mg/g |
|---|---|
| Example 1 | |
| Ointment | |
| Active Ingredient | 10.0 |
| Acetone | 180.0 |
| SD Alcohol 40 | 360.0 |
| Mineral Oil | 50.0 |
| White Petroleum q.s. ad | 1.0 |
| Example 2 | |
| Lotion | |
| Active Ingredient | 10.0 |
| Acetone | 180.0 |
| SD Alcohol 40 | 360.0 |
| Polyethylene glycol 400 | 100.0 |
| Hydroxypropyl cellulose | 5.0 |
| Propylene glycol q.s. ad | 1.0 |
| Purified Water q.s. ad | 100.0 |
| Example 3 | |
| Cream | |
| Active Ingredient | 10.0 |
| Acetone | 180.0 |
| SD Alcohol 40 | 360.0 |
| Isopropyl myristate | 100.0 |
| Polyoxyethylene (2) monostearyl ether | 10.0 |
| Polyoxyethylene (20) monostearyl ether | 25.0 |
| Propylene glycol | 100.0 |
| Purified water q.s. ad | 1.0 g |
| Example 4 | |
| Gel | |
| Active Ingredient | 10.0 |
| Acetone | 180.0 |
| SD Alcohol 40 | 360.0 |
| Hydroxypropyl cellulose | 50.0 |
| Allantoin | 10.0 |
| Propylene glycol | 50.0 |
| Purified water q.s. ad | 1.0 g |
| Example 5 | |
| Suspension | |
| Active Ingredient | 10.0 |
| Acetone | 180.0 |
| SD Alcohol 40 | 360.0 |
| Polyethylene glycol 400 | 100.0 |
| Hydroxypropyl cellulose | 5.0 |
| Propylene glycol q.s. ad | 1.0 |
| Example 6 | |
| Emulsion | |
| Active Ingredient | 10.0 |
| Acetone | 180.0 |
| SD Alcohol 40 | 360.0 |
| Polyethylene glycol 400 | 100.0 |
| Hydroxypropyl cellulose | 5.0 |
| Propylene glycol q.s. ad | 1.0 |

I claim:

1. A method of topically treating bacterial infections of the skin caused by susceptible organisms which comprises administering to an individual a composition of a fluoroquinolone antibiotic present in a vehicle containing acetone and alcohol, applied directly to the affected areas of the human skin.

2. The method described in claim 1 wherein the fluoroquinolone antibiotic is selected from a group consisting of ciprofloxacin, ofloxacin, enoxacin, cinoxacin, pefloxacin, lomefloxacin, norfloxacin, tosufloxacin, flerxacin, temafloxacin, trovafloxacin, and difloxacin, in a topical agent, in the form of an ointment, cream, lotion, gel, suspension, emulsion, cleansing bar, pledget, salve, tincture, spray, transdermal device, or other appropriate non-toxic pharmaceutical carrier.

3. The method described in claim 1 wherein the fluoroquinolone antibiotic is present in a range from about 5% to about 10% by weight of the composition.

4. The method described in claim 1 wherein the alcohol and acetone is present in a weight percent from 0.1% to 95.0%.

5. A method described in claim 1 wherein the topical carrier is present in a weight percent from 75.0% to 94.9%.

* * * * *